(12) United States Patent
Noda et al.

(10) Patent No.: US 6,566,582 B1
(45) Date of Patent: May 20, 2003

(54) ANIMALS WITH INSUFFICIENT EXPRESSION OF URIDINE PHOSPHORYLASE

(75) Inventors: Tetsuo Noda, Tokyo (JP); Hiroaki Tsujimoto, Iruma (JP); Masakazu Fukushima, Hannou (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/890,971

(22) PCT Filed: Dec. 15, 2000

(86) PCT No.: PCT/JP00/08898

§ 371 (c)(1),
(2), (4) Date: Aug. 8, 2001

(87) PCT Pub. No.: WO01/43539

PCT Pub. Date: Jun. 21, 2001

(30) Foreign Application Priority Data

Dec. 17, 1999 (JP) ............................................. 11-359796

(51) Int. Cl.$^7$ ...................... A01K 67/027; C12N 15/00; C07H 21/04
(52) U.S. Cl. ............................... 800/3; 800/18; 800/22; 536/23.1
(58) Field of Search ................................ 800/18, 3, 22; 435/183; 536/23.1

(56) References Cited

FOREIGN PATENT DOCUMENTS

WO    WO 01/60985    8/2001

OTHER PUBLICATIONS

Sigmund, Viewpoint: Are studies in genetically altered mice out of control?, 2000, Thromb. Vasc. Biol., vol. 20, pp. 1425–1429.*
Watanabe et al., Purification, cloning, and expression of murine uridine, 1995, The Journal of Biological Chemistry, vol. 270, pp. 12191–12196.*
Mansour et al., Disruption of the proto–oncogene int–2 in mouse embryo–derived stem cells: a general strategy for targeting mutations to non–selectable genes, 1988, Nature, vol. 336, pp. 348–352.*
Osterrieder et al., Lessons from gene knockouts, 1998, Rev. Sci. Tech. Off. Int. Epiz., vol. 17, pp. 351–364.*
D. Cao, et al., Proceedings of the American Association for Cancer Research Annual Meeting, vol. 40, p. 8, XP–001064199, "Construction of Uridine Phosphorylase Knockout Cell Lines: Effect on Pyrimidine Pools and 5–Fluorouracil Antitumor Activity", Mar. 1999.
Shin–Ichi Watanabe, et al., The Journal of Biological Chemisty, vol. 270, No. 20, pp. 12191–12196, "Purification, Cloning, and Expression of Murine Uridine Phosphorylase", May 19, 1995.
Mario R. Capecchi, Science, vol. 244, pp. 1288–1292, "Altering the Genome by Homologous Recombination", Jun. 16, 1986.
Ken–ichi Yamamura, Idenshi Iryou, vol. 2, No. 4, pp. 612–617, "Gene Trapping", 1998.
Suzanne L. Mansour, et al., Proc. Natl. Acad. Sci. USA, vol. 87, pp. 7688–7692, "Introduction of a Lacz Reporter Gene into the Mouse Int–2 Locus by Homologous Recombination", Oct. 1990.
Richard D. Palmiter, et al., Nature, vol. 300, pp. 611–615, "Dramatic Growth of Mice that Develop from Eggs Microinjected with Metallothionein–Growth Hormone Fusion Genes", Dec. 16, 1982.
Shin–Ichi Watanabe, et al., Biochemical and Biophysical Research Communications, vol. 216, No. 1, pp. 265–272, "Cloning and Expression of Human Uridine Phosphorylase", Nov. 2, 1995.

* cited by examiner

*Primary Examiner*—Ann-Marie Falk
*Assistant Examiner*—Celine Qian
(74) *Attorney, Agent, or Firm*—Oblon, Spivak, McClelland, Maier & Neustadt, P.C.

(57) ABSTRACT

Non-human animals deficient in a function of a uridine phosphorylase gene on a chromosome, and their offspring. These non-human animals and their offspring make it possible to elucidate pathologic functions and activities of nucleic acid dysbolism and the like and also to predict utility of pyridine nucleoside antimetabolites in human, and are useful as experimental animals.

8 Claims, 5 Drawing Sheets

UP-LacZ596 — WILD TYPE LOCUS (10kb) / LacZ MUTANT LOCUS (6.1kb)

FIG. 4b

UP-LacZ658 — WILD TYPE LOCUS (10kb) / LacZ MUTANT LOCUS (6.1kb)

FIG. 4c

UP-neo32 — WILD TYPE LOCUS (10kb) / Neo MUTANT LOCUS (5.1kb)

FIG. 5

ANIMALS WITH INSUFFICIENT EXPRESSION OF URIDINE PHOSPHORYLASE

TECHNICAL FIELD

This invention relates to non-human animals deficient in the expression of uridine phosphorylase, and also to their offspring.

BACKGROUND ART

Pyrimidine nucleoside phosphorylases are enzymes, which take part in the biosynthesis and degradation of pyrimidine in its metabolism and play an important role of regulating the in vitro nucleoside pool through degradation and synthesis of pyrimidine bases in the salvage pathway. Further, pyrimidine nucleoside phosphorylases in mammals are known to include uridine phosphorylase and thymidine phosphorylase, both of which take part in the biosynthesis and degradation in its metabolism. Concerning such pyrimidine nucleoside phosphorylase genes, cDNAs have been isolated from mice and human, and elucidation of their differences in expression is now under way on the gene level [Uchida et al., J. Biol. Chem., 270, 12191–19196 (1995); Uchida et al., Biochem. Biophys. Res. Commun., 216, 265–272 (1995)].

On the other hand, nucleoside antimetabolites which are playing an important role in the field of cancer chemotherapy in recent years are known to be inactivated by pyrimidine nucleoside phosphorylase due to their chemical structures. For the development of drugs excellent in pharmacological effects and low in side effects, it is therefore considered to be necessary to accurately grasp the mechanism of metabolism of these substances by pyrimidine nucleoside phosphorylase.

Uridine phosphorylase and thymidine phosphorylase are, however, observed to have substantial differences in their distribution depending on species. In human, thymidine phosphorylase are expressed in both normal tissues and tumor tissues, whereas in rodents such as mice and rats, uridine phosphorylase is primarily expressed centering around digestive tracts and thymidine phosphorylase is expressed only in some tissues such as livers. This has led to a problem in that the utility and the like of nucleoside anticancer agents in human cannot be precisely predicted from data on rodents.

On the other hand, thymidine phosphorylase is known to function as an angiogenic factor. It has recently been identified as a causative gene of MNGIE, a mitochondrial disease.

Accordingly, uridine phosphorylase expression deficient animals, if available in a phyletic lineage, will be useful as experimental animals for the study of physiological functions of the protein, for the elucidation of its related diseases, and also for the development and research of pyridine nucleoside antimetabolites (anticancer agents).

An object of the present invention is to provide a uridine phosphorylase expression deficient non-human animal or its offspring, which can be used as an experimental animal.

DISCLOSURE OF THE INVENTION

With the foregoing current circumstances in view, the present inventors have proceeded with research in various ways on mutation of a uridine phosphorylase gene, designing of a targeting vector, and so on. As a result, the present inventors have succeeded in creating a transformed animal having a uridine phosphorylase gene which practically does not function, and its offspring, leading to the completion of the present invention.

Specifically, the present invention provides a non-human animal deficient in a function of a uridine phosphorylase gene on a chromosome, or an offspring thereof.

As a result of developments in genetic engineering in recent years, it has become possible to artificially manipulate various genes and to create various transformed animals artificially added with foreign genetic characteristics or controlled in the expression of genetic characters which the organisms inherently possess [Nature, 300, 611–615 (Dec. 16, 1982); Proc. Natl. Acad. Sci. USA, 87, 7688–7692 (October 1990), etc.]. However, animals which are deficient in the function of a uridine phosphorylase gene on a chromosome and are genetically stable are not known to date.

BEST MODES FOR CARRYING OUT THE INVENTION

The expression "deficient in a function of a uridine phosphorylase gene on a chromosome" as used herein means that a uridine phosphorylase gene on a chromosome in a somatic cell or a germ cell is different from its original structure by deletion of a part of its base sequence, insertion of or replacement with another gene, or the like and cannot produce a protein capable of functioning as uridine phosphorylase or even if a genetic product is obtained, its protein cannot function as uridine phosphorylase; and specifically, indicates destruction of the function by gene mutation, such as deletion, insertion or replacement, of the base sequence of a promoter region or coding region.

The term "non-human animal deficient in a function of a uridine phosphorylase gene on a chromosome", therefore, means a uridine phosphorylase expression deficient animal created by modifying (manipulating) a uridine phosphorylase gene (mutant uridine phosphorylase gene) in accordance with a genetic engineering procedure.

The "non-human animal" can be any animal having a uridine phosphorylase gene other than human, although a non-human mammal. Examples of the non-human mammal can include bovines, pigs, sheep, goats, rabbits, dogs, cats, guinea pigs, hamsters, mice, and rats. Among these, rodents featuring relatively short ontogenesis and reproduction cycle and easy breeding, especially mice and rats are preferred from the standpoint of preparation of a morbid animal model line.

For the disruption of a uridine phosphorylase gene on a chromosome, it is possible to apply methods which are commonly used for disrupting genes on chromosomes. Specifically, the function of the uridine phosphorylase gene in an animal and its offspring can be rendered deficient by cloning the uridine phosphorylase gene to delete the function of the gene in vitro and then introducing the deficient gene back into the animal.

Illustrative of methods for introducing a gene into animals are (1) injection of genetic DNA into the embryo of a germ cell in its prokaryotic stage, (2) transfection of an early embryo with a recombinant retrovirus, and (3) injection of an embryo-derived stem cell (ES cell), which has been caused to undergo homologous recombination, into a blastocyst or into an embryo in its eight cell stage. These methods are all usable for the provision of the non-human animal according to the present invention. Nonetheless, the gene introduction method making use of an ES cell is preferred in that it is suited for disrupting a gene by homologous recombination and its permits conducting the introduction of the ES cell into the gene and the creation of a chimeric animal as separate steps.

Therefore, as the non-human animal according to the present invention, a chimeric animal can firstly be created by forming a cell having a mutant uridine phosphorylase gene (for example, an ES cell) and transplanting the cell into an animal; and further, an animal in which the mutant uridine phosphorylase gene is heterogeneously or homogeneously deleted in all the constituent cells thereof can be created by mating the chimeric animal with a different individual.

A description will hereinafter be made in detail about a representative method for the production of the non-human animal and its offspring according to the present invention.

Figure 1:
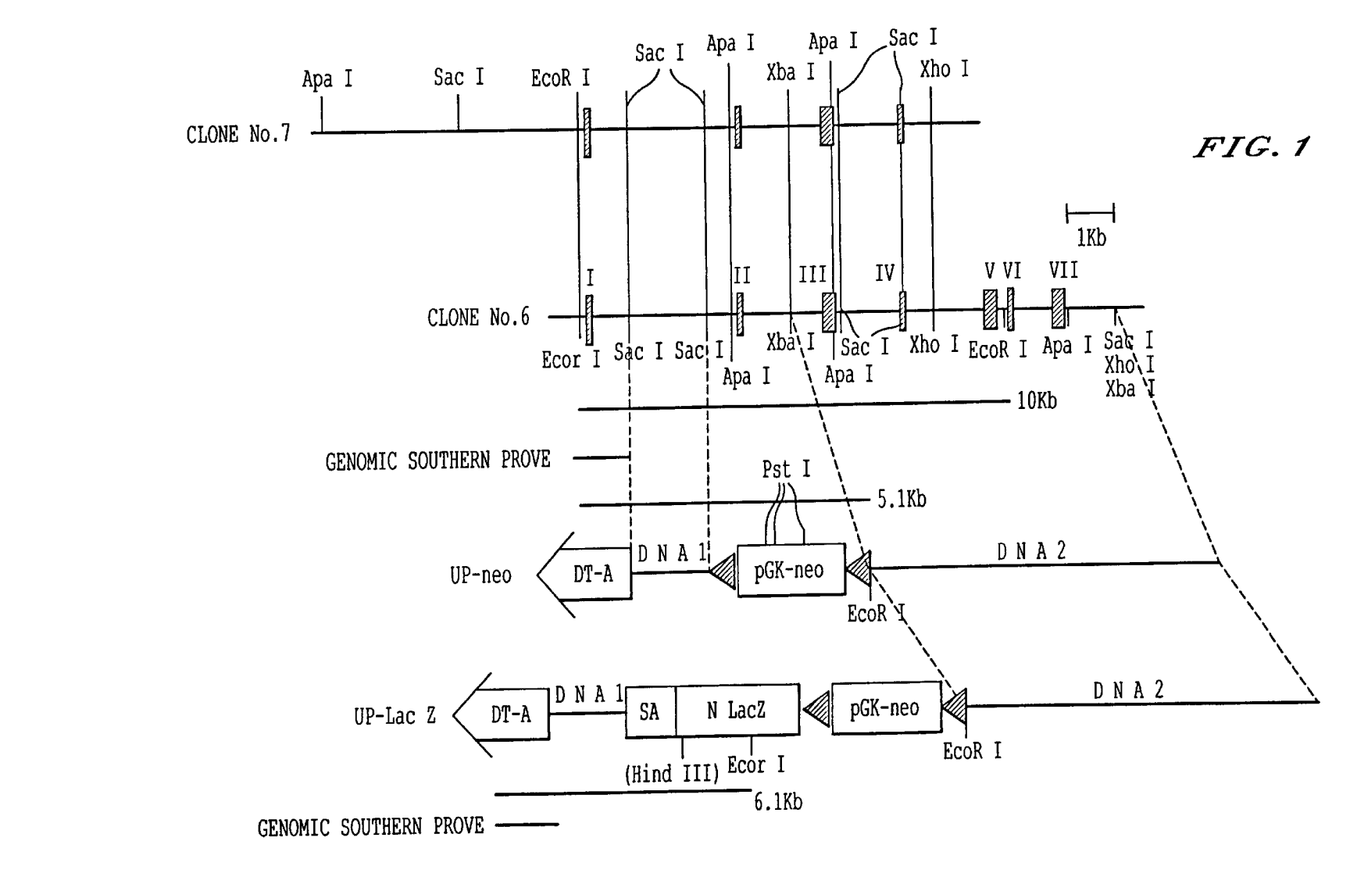
FIG. 1 is a schematic representation of a mouse uridine phosphorylase gene and its targeting disruption. In the representation, neo represents a neomycin-resistant gene, DT-A represents the gene of fragment A of diphtheria toxin, LacZ represents a β-galactosidase gene, thick solid lines represent exons, and fine solid lines represent introns.
Figure 2:
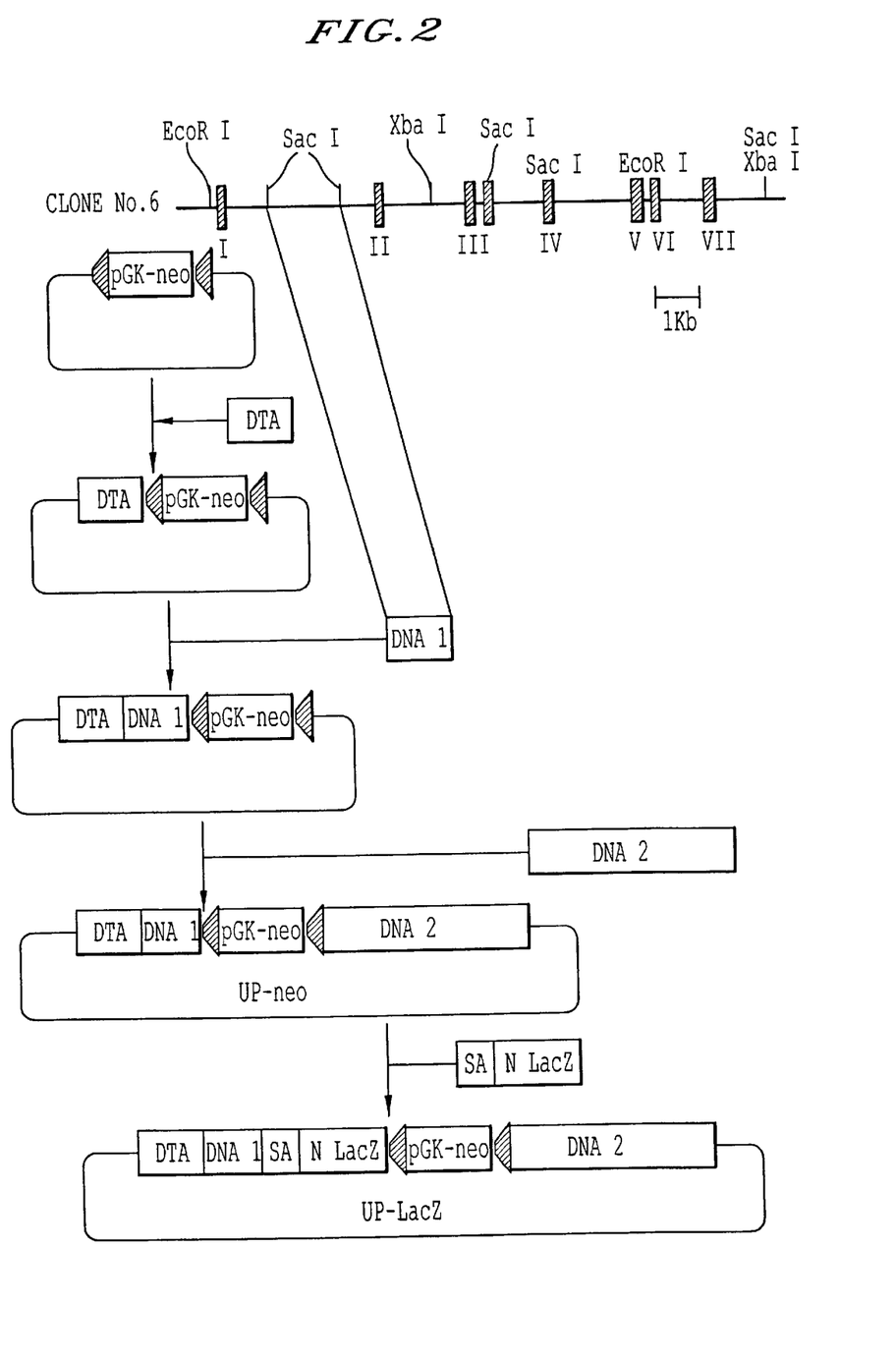
FIG. 2 is a construction scheme of a targeting vector for the mouse uridine phosphorylase gene. In the scheme, neo represents the neomycin-resistant gene, DT-A represents the gene of fragment A of diphtheria toxin, LacZ represents the β-galactosidase gene, thick solid lines represent exons, and fine solid lines represent introns.

A mutant of a uridine phosphorylase gene (mutant uridine phosphorylase gene) is obtained by deleting a part of the base sequence of the uridine phosphorylase gene, inserting another gene into the base sequence or replacing a part of the base sequence with another gene. No particular limitation is imposed on a position at which the deletion, insertion or replacement is to be effected, insofar as it is such a position that the deletion, insertion or replacement makes it impossible to obtain any functioning genetic product. The position can be in any region such as a promoter region, an intron region, an exon region or the like. To assure the deletion of the expressing ability of the gene, it is preferred to mutate at least a part of the promoter region or the coding region. It is also possible to insert another gene such as a reporter gene into the deleted, substituted or inserted position. For example, the uridine phosphorylase gene of a mouse, as illustrated in FIG. 1 and FIG. 2, contains 7 coding exons and a uridine phosphorylase protein is coded over the 7 coding exons. For the deletion of the expressing ability of the uridine phosphorylase gene, it is, therefore, possible to delete one or some of these exons or to insert another gene at any one of the positions of these exons.

The uridine phosphorylase gene can be either a genome-derived uridine phosphorylase gene isolated or extracted from an animal or cDNA cloned using a genetic engineering procedure. The cloned uridine phosphorylase gene can be obtained by extracting genomic DNA, for example, from the liver of a mouse, preparing a genomic DNA library from the genomic DNA by a method known per se in the art, and screening the DNA library while using as a probe a partial sequence of pre-cloned DNA which codes uridine phosphorylase mRNA, for example, cDNA [in the case of a mouse, Uchida et al., J. Biol. Chem., 270, 12191–12196 (1995)].

Application of an artificial mutation to the above-described uridine phosphorylase gene can be conducted in vitro by usual DNA recombination technology.

When destroying the function of an exon by inserting a reporter gene, it is preferred to insert the reporter gene such that the function of the exon may be expressed under control of a promoter or in a form combined with the gene. The term "reporter gene" as used herein indicates a group of genes, each of which can serve as an index of expression of the gene. In general, structural genes of enzymes which catalyze a photogenic reaction or chromogenic reaction are often used. The reporter gene makes it possible to investigate not only whether the introduced gene has been expressed in cells but also which tissue it has been expressed in. Specifically, lacZ (*Escherichia coli* β-galactosidase gene), cat (chloramphenicol acetyltransferase gene) or the like is used.

Next, a targeting vector is prepared for homologous recombination to delete the function of the uridine phosphorylase gene.

The targeting vector can be designed by deleting the chromosome-derived uridine phosphorylase gene either in part or in its entirety, inserting another base sequence into the uridine phosphorylase gene or replacing a part of the uridine phosphorylase gene with another base sequence such that the upstream and downstream regions flanking the mutated part have homologous base sequences as the uridine phosphorylase gene.

The targeting vector can also be designed in such a way that, when a reporter gene is inserted in the targeting vector, the base sequence of the reporter gene is contained in the non-homologous part of the base sequence of the targeting vector.

Further, the targeting vector may preferably be inserted with marker genes permitting selection of vector-incorporated cells or cells having high possibility of having undergone intended homologous recombination, for examples, a gene widely employed for the selection of drug, such as neomycin-resistant gene (neo), a herpes simplex virus thymidinekinase gene (HSV-tk), or a thymidinekinase gene (tk). For example, the neomycin resistant gene makes it possible to select a target gene by using G418, a neomycin analogue. It is also possible to use, along with a positive selection marker gene such as the neomycin resistant gene (neo), a marker gene useful for negative selection to selectively remove a target cell, for example, a thymidinekinase gene (tk) (ganciclovir, FIAU or the like is used as a selecting agent, and depending on the sensitivity to the selecting agent, a non-homologous recombinant is selectively removed) or the diphtheria toxin fragment A (DT-A) gene (a non-homologous recombinant is selectively removed by diphtheria toxin expressed by DT-A).

Preparation of such a targeting vector can be conducted by conventional DNA recombination technology. For example, a cloned uridine phosphorylase gene is used. This gene is digested with a suitable restriction enzyme to obtain a fragment, or is partially amplified by PCR to prepare a DNA fragment. The fragment or DNA fragment can then be linked to a linker DNA synthesized by a DNA synthesizer, a fragment containing a reporter gene, a fragment containing a drug-resistance marker gene and the like in a desired order in accordance with a design as described above.

The homologous recombinational targeting vector prepared as described above is next introduced into a suitable cell commonly employed for the creation of a chimeric animal.

Examples of the cell employed here can include an ovule and an embryo-derived stem cell (ES cell), although an ES cell is preferred in that is equipped with pluripotency sufficient to differentiate into all kinds of cells in an organism. The introduction of the vector DNA into the cell can be carried out by a conventional method, for example electroporation, microinjection or calcium phosphate transfection.

An ES cell has been established from an inner cell mass of a mouse blastocyst of 129 cell line, and is a cell line growth and culture of which is feasible while maintaining its undifferentiated state. Concerning mice, a method has been established for introducing a gene by using an ES cell [Mansour, S. L., et al., Nature, 336, 348 (1988)]. Theoretically, culture of an ES cell is considered to be feasible in all species of mammals, and research is currently under way to also establish ES cells with respect to J rats, rabbits, and cattle, such as pigs and bovines, in addition to mice. Incidentally, for animal species ES cells of which are not cultured or are cultured but have not been established to such cell lines as differentiating to germ cells, mutant genes can be introduced by the above-described method (1) or (2) or a like method.

The mutant uridine phosphorylase gene of the targeting vector can be introduced into an animal by replacing a uridine phosphorylase gene on a chromosome in a cell (for example, an ES cell) of the animal with the base sequence of the mutant uridine phosphorylase gene of the targeting vector in accordance with homologous gene recombination. At this time, the marker gene and reporter gene inserted in the targeting vector DNA are inserted in the uridine phosphorylase gene in the genome of the ES cell.

In the cell with the targeting vector incorporated therein, the marker gene, such as a drug resistant gene, in the vector DNA has also been inserted at the same time so that by culturing the cell for an appropriate period, for example, in the presence of the drug, the cell can be selected based on the expression of the gene. Among cells so selected, those having undergone mutation by the homologous recombination can be determined by an analysis making use of Southern hybridization in which the DNA sequence on or adjacent to the uridine phosphorylase gene is used as a probe or by an analysis making use of PCR in which the DNA sequence on the targeting vector and a DNA sequence in an adjacent region other than the mouse-derived uridine phosphorylase gene employed in the targeting vector are used as primers.

Using the cell with the mutated uridine phosphorylase locus occurred therein, a chimeric animal is next created in accordance with a procedure which is generally used for the creation of chimeric animals such as injection, cell aggregation or the like.

Described specifically, a chimeric animal—which is composed of cells having the normal uridine phosphorylase focuses and cells having the mutated uridine phosphorylase locuses—can be obtained by injecting a cell (for example, an ES cell) with the mutated locus occurred therein into a non-human animal embryo or blastocyst in an appropriate early stage of embryo formation, for example, in its 8-cell stage and transplanting the resulting embryo in the uterus of a pseudocyetic animal. Selection as to what line of animal a host embryo is to be obtained from should be made such that cells to be derived from the ES cell and those to be derived from the host embryo would be successfully distinguished depending on a phenotype such as fur colors in accordance with a usual method.

When some of germ cells of the chimeric animal have the mutant uridine phosphorylase locuses, individuals the tissues of which are all composed of cells having the mutant uridine phosphorylase locuses (uridine phosphorylase expression deficient animals) can be selected by a discrimination method, which relies upon the fur color or the like, from a group of individuals obtained by mating a chimeric individual with a normal individual.

When a chimeric mouse obtained using, for example, a mouse ES cell of the J1 strain and a host embryo of the C57BL/J line is mated with a C57BL/6J-line mouse, offspring to be ejected will present the same wild color (agouti) as the mouse from which the ES cell was derived if germ cells of the chimeric mouse are derived from the recombinant ES cell, but present the same black color as the mouse from which the host embryo was derived if the germ cells of the chimeric mouse ware derived from the host embryo. The deleted expression of the uridine phosphorylase gene can be confirmed by performing Southern blot or PCR analysis of tail DNA from new born and fed mice.

Further, mating between F1 heterozygous expression deficient offspring themselves makes it possible to obtain both F2 heterozygous expression deficient offspring and F2 homozygous expression deficient offspring. Non-human animals according to the present invention can embrace chimeric animals, F1 heterozygous expression deficient animals and F2 homozylous expression deficient animals. F2 homozylous expression deficient animals are, however, preferred from the standpoint of effects of the expression deficiency of the uridine phosphorylase gene.

Transformed non-human animals obtained as described above are deficient in the ability to express uridine phosphorylase genes on chromosomes in somatic cells and germ cells, and the deficiency is genetically stable.

EXAMPLES

The present invention will hereinafter be described specifically based on Examples.

Example 1

Preparation of Targeting Vector of the Mouse Uridine Phosphorylase Gene DNA

A recombinant phage library of lambda FIXII with genomic DNA of a 129SV mouse liver liked thereto (product of Stratagene LLC) was obtained and transfected to *Escherichia coli* LE392. With respect to the resulting mouse genomic library, hybridization was conducted using cDNA of the mouse uridine phosphorylase gene as a probe [Uchida et al., J. Biol. Chem., 270, 12191–12196 (1995)]. As a result of screening on $1\times10^6$ plaques, 2 positive clones were obtained (FIG. 1: clone No. 7 and clone No. 6). Using these, an approx. 1.8 kb SacI-SacI fragment containing intron 1 of the uridine phosphorylase gene (FIG. 1: DNA 1) and an approx. 7.0 kb XbaI-XbaI fragment containing exons 3–7 (FIG. 1: DNA 2) were subcloned.

Next, preparation of a targeting vector for disrupting the structure of the uridine phosphorylase gene was conducted.

A neomycin resistant gene (pGK-neo) was inserted into pBluescrptIISK(+), and the diphtheria toxin fragment A gene (DT-A) was inserted in a direction opposite to the normal direction of its transcription on the upstream 5'-end side. Further, the approx. 1.8 kb SacI-SacI fragment with intron 1 of the uridine phosphorylase gene contained therein (FIG. 1: DNA 1) was inserted as a segment homologous to the genomic DNA between pGK-neo and DT-A, and the approx. 7.0 kb XbaI-XbaI fragment with coding exons 3–7 contained therein (FIGS. 1 and 2: DNA 2) was inserted on the downstream 3' side of pGK-neo. As a result, UP-neo (FIGS. 1 and 2) was obtained. Furthermore, an SA-NLacZ gene with a splicing acceptor (SA) and a nuclear transport signal added thereto was inserted as an expression-analyzing reporter gene between DNA1 and pGK-neo to obtain UP-LacZ (FIGS. 1 and 2). Upon introduction into ES cells, the constructs were both digested and linearized with a restriction enzyme NotI to obtain targeting vectors.

Example 2
Deletion of the Uridine Phosphorylase Gene from ES Cells by the Introduction of DNA for Homologous Recombination The two kinds of DNAs for homologous recombination (UP-neo and UP-LacZ; 25 µg, each) were separately suspended in aliquots of an electroporating buffer, each of said aliquots containing $2 \times 10^7$ mouse ES cells (J1 strain), and under conditions of 400 V/cm field strength and 25 µF capacitance, gene introduction was conducted. Selective incubation was conducted at a G418 ("Genetisin", product of GIBCO BRL) concentration of 175 µg/mL from the $46^{th}$ hour after the introduction of UP-neo and from the $44^{th}$ hour after the introduction of UP-LacZ, respectively.

Each G418 colony was transferred to a 96-well microplate, each well of which contained 0.05% trypsin-HBS-EDTA solution (40 µL), by a micropipet from the $184^{th}$ hour after the introduction of the corresponding gene. After the colony was treated for 5 minutes, it was pipetted to provide single cells. Those single cells were halved, and were then transferred to 96-well microplates, followed by incubation. After sufficient proliferation, they were transferred to 24-well microplates and incubated further. A half of the cells was stored in liquefied nitrogen, while the remaining half of the cells used for extracting DNA to be used for the detection of a recombinant by Southern hybridization.

The DNA extraction was conducted by a method known per se in the art. As the samples were many, DNA precipitated by ProteinaseK treatment and isopropanol treatment was digested by EcoRI, followed by Southern hybridization. As a probe, an approx. 1.3 kb EcoRI-SacI fragment situated further upstream of the 5'-side homologous region employed as the targeting vector was used as illustrated in FIG. 1. When detected by Southern hybridization, use of that probe was expected to result in the appearance of a band at 10 kb in the case of the non-homologous recombinant ES cells, at 5.1 kb in the case of the ES cells undergone homologous recombination by UP-neo because of the introduction of EcoRI-digested sites upon insertion of the neomycin resistant gene, or at 6.1 kb in the case of UP-LacZ.

Figure 3:
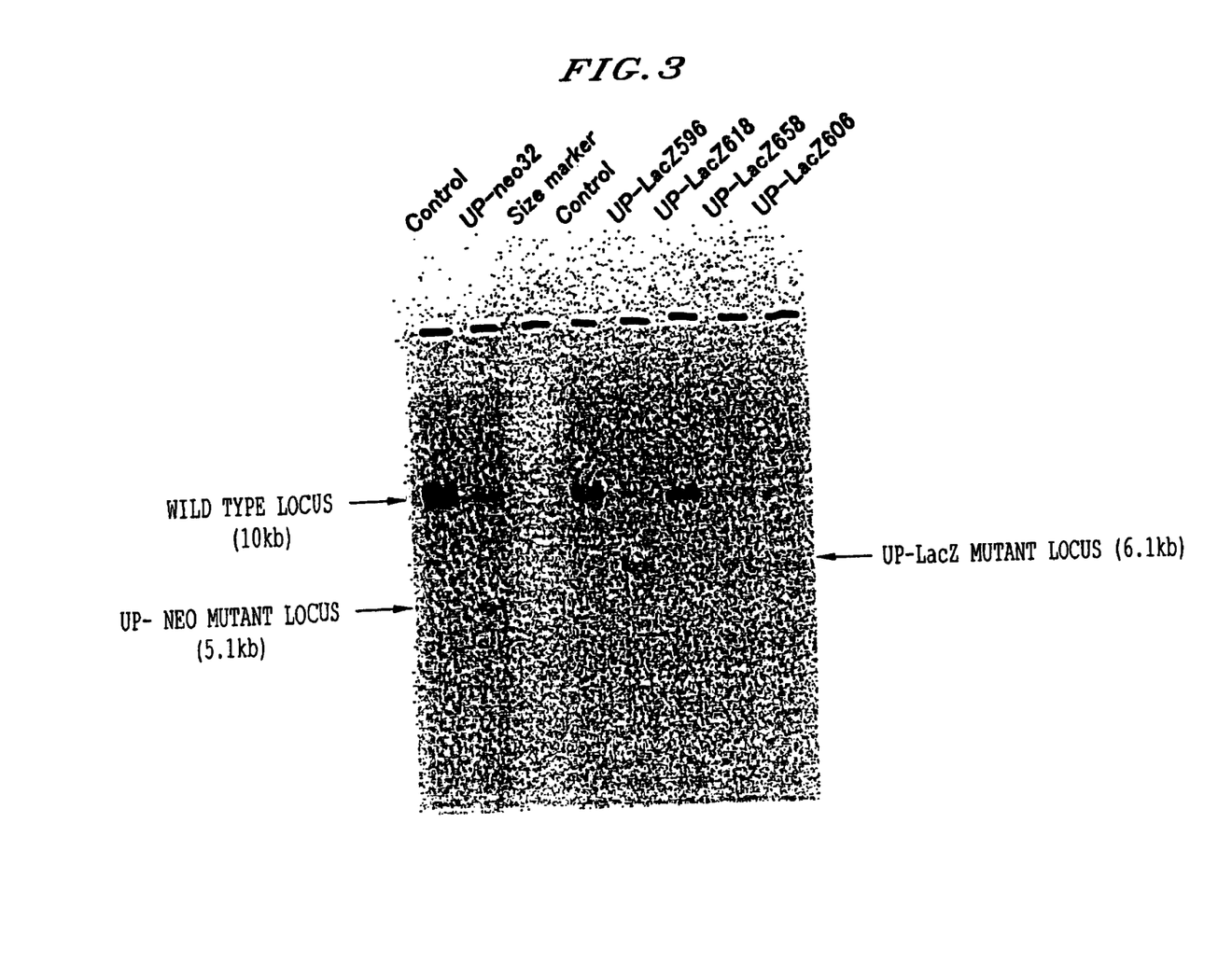
FIG. 3 illustrates electrophoresis patterns showing the results of genomic Southern hybridization which was conducted for the confirmation of homologous recombinant ES cells.

The results of the hybridization were analyzed by Bio-Image Analyzer BAS2000 (Fuji). As the frequency of homologous recombination, 1 out of 70 clones underwent homologous recombination in the case of UP-neo, while 4 out of 135 clones underwent homologous recombination in the case of UP-LacZ (FIG. 3). A cell, bands of a mutant locus and a wild locus in which appeared at substantially the same intensity, was selected and introduced in a blastocyst.

Example 3
Creation of Chimeric Mice and Selection of Uridine Phosphorylase Expression Deficient Mouse A chimeric mouse was prepared by the method reported by Bradley et al. [Bradley, A., Production and analysis of chimeric mice in teratocarcinomas and embryonic stem cells; A practical approach. E. J. Roberson ed. (Oxford: IRL press), 113–151(1987)] or by the method proposed by Gossler et al. [Gossler, A., Doetschman, T., Korn, R., Serfling, E., and Kemler, R., Transgenesis by means of blastocyst-derived embryonic stem cell lines, Proc. Natl. Acad. Sci. USA, 83, 9065–9069 (1986)]. On the $3.5^{th}$ day after copulation with C57BL/6, a blastocyst was obtained from the oviduct, and in its cavity, about 7 homologous recombinant ES cells were injected. The blastocyst with the ES cells injected therein was returned to the uterus of a pseudopregnated ICR mouse. From chimeric mice born from the foster mother, two mice with a fur color lightened from the inherent black color, said fur color lightening being presumably attributable to a large contribution by the ES cell, were selected, and those selected mice were allowed to mate with C57BL/6. For an agouti colored one of newly born mice, Southern blot analysis of tailed DNA was performed by the general method. After treated with proteinase K, the DNA in the tail tissue was extracted with chloroform, precipitated in ethanol, and then dissolved in TE solution. Mice having locuses, which had undergone recombination, were selected, and were allowed to mate with each other to obtain mice having homozygous recombinant uridine phosphorylase locuses.

Figure 4A:
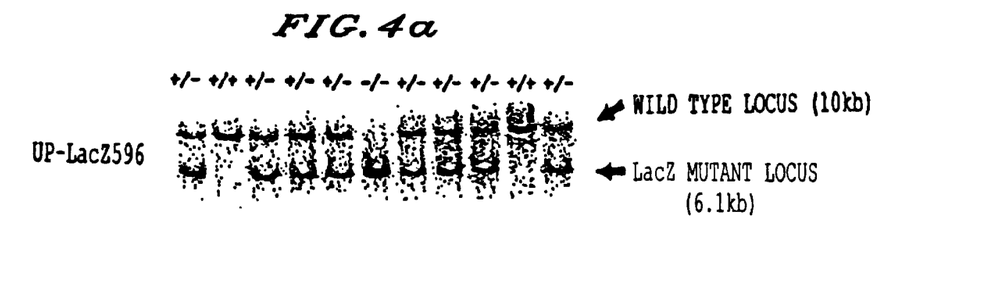
FIG. 4 illustrates electrophoresis patterns showing the results of genomic Southern hybridization which was conducted for the confirmation of a homologous recombinant mouse. In the electrophoresis patterns, +/+ indicates a normal mouse, +/− indicates a heterozygous deficiency mouse, and −/− indicates a homozygous deficiency mouse.
Figure 4B:
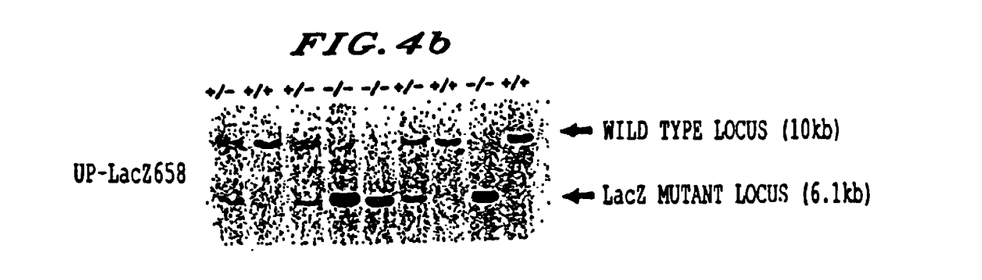
Figure 4C:
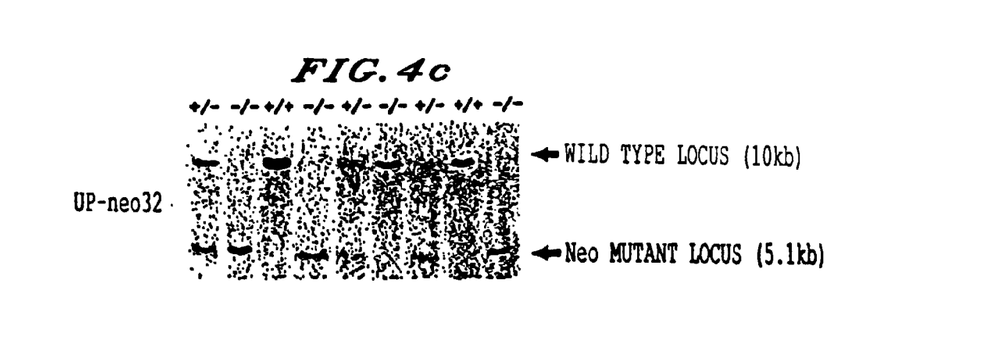

Using the 1.3 kb EcoRI-SacI fragment as a probe, Southern hybridization was then conducted. Bands appeared at 6.1 kb and 10 kb, respectively, so that uridine phosphorylase on one of the chromosomes was determined to have been destroyed. Twenty-one (21) mice of the agouti color were obtained concerning UP-neo, while 36 mice of the agouti color were obtained with respect to UP-LacZ. When analyzed by Southern hybridization, 11 UP-neo mutant mice showed bands at 5.1 kb and 10 kb, respectively, and 16 UP-LacZ mutant mice presented bands at 6.1 kb and 10 kb, respectively. Those mice were then allowed to mutually mate. Eventually, UP-neo mutant mice showing a band only at 5.1 kb and UP-LacZ mutant mice presenting a band only at 6.1 kb, that is, mice having homozygous mutant uridine phosphorylase locuses were obtained (FIG. 4). Mice so born did not show any appreciable abnormality. It has therefore been determined that such mice are born absolutely healthy. As mice having gene types of UP +/+, +/− and −/− were born at a ratio of approx. 1:2:1 between the litter mates, it has also been determined that UP −/− mice are also born absolutely healthy irrespective of the genetic background.

Example 4
Uridine Phosphorylase Activity in Normal and Mutant Mice

Mice having homozygous mutant uridine phosphorylase genes were investigated for the existence or non-existence of uridine phosphorylase activity. Briefly, small intestine and liver tissues from uridine phosphorylase deficient mice and parental mice (normal) as a control, showing full expression of uridine phosphorylase gene, were isolated and homogenized with 4 volumes of a buffer (50 mM Tris-HCl, 10 mM 2-mercaptoethanol, 25 mM KCl, 5 mM $MgCl_2$). Subsequent to centrifugation under 105,000 g for 60 minutes, the activity was measured using its supernatant. Uridine phosphorylase activity was measured based on [$^3$H]uridine formed from [$^3$H]uracil by the method reported by Ikenaka et al. [Ikenaka et al., Metabolism of pyrimidine nucleotides in various tissues and tumor cells from rodents. Gann. 72(4), 590-7 (August, 1981)]. At the same time, the activity of thymidine phosphorylase, the other enzyme in the pyrimidine nucleoside phosphorylase group, was also measured based on [$^3$H]thymine formed from [$^3$H]thymidine. The results are presented-in Table 1.

TABLE 1

| Mice | n | Uridine phosphorylase activity[1] (nmol/min/mg protein) | | Thymidine phosphorylase activity[2] (nmol/min/mg protein) | |
|---|---|---|---|---|---|
| | | Small intestine | Liver | Small intestine | Liver |
| Non-recombinant (normal) mice | 15 | 20.99 ± 8.18 | 0.27 ± 0.12 | 2.31 ± 0.94 | 1.11 ± 0.06 |
| Uridine phosphorylase expression deficient mice | 15 | 0.44 ± 0.19 | 0.04 ± 0.05 | 0.68 ± 0.40 | 1.01 ± 0.58 |

[1] Measured based on [$^3$H] uracil formed from [$^3$R] uridine.
[2] Measured based on [$^3$H] thymine formed from [$^3$H] thymidine.

As a result, the uridine phosphorylase activity in the small intestine tissue was high in the non-recombinant (normal) mice but was markedly reduced and lost in the uridine phosphorylase expression deficient mice. In the liver tissues of the normal mice, uridine phosphorylase activity was low but thymidine phosphorylase was expressed high. In the uridine phosphorylase expression deficient mice, on the other hand, uridine phosphorylase activity was substantially lost in the liver tissues.

Figure 5:
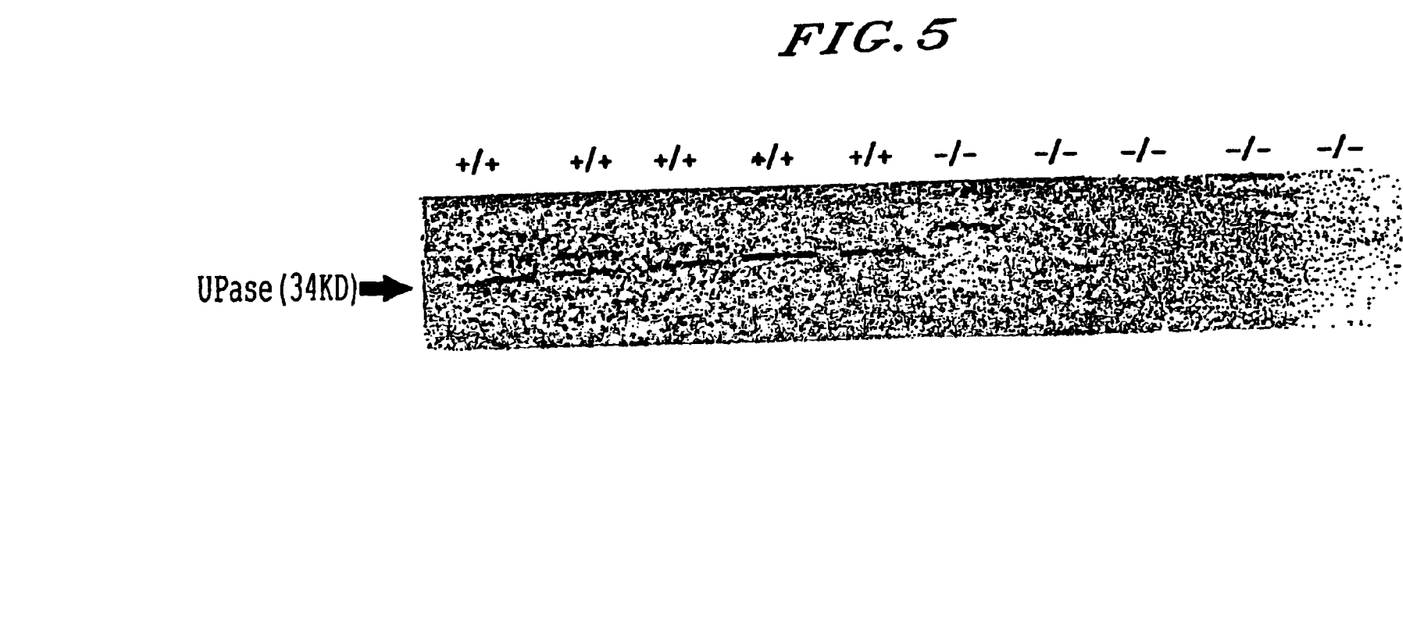
FIG. 5 illustrates electrophoresis patterns showing expression levels of uridine phosphorylase by normal mice and uridine phosphorylase expression deficient mice. In the electrophoresis patterns, +/+ indicates a normal mouse, and −/− indicates a homozygous deficiency mouse.

Example 5
Expression of Uridine Phosphorylase Protein in the Small Intestines of Normal and Uridine Phosphorylase Expression Deficient Mice From 5 normal mice and 5 uridine phosphorylase expression deficient mice, small intestine tissues were enucleated, respectively. From each small intestine tissue, a protein extract was prepared in accordance with the above-described procedure. The protein extract was adjusted to a protein content of 5 mg/mL, and was investigated for the expression of uridine phosphorylase protein by Western blotting. For the detection, anti-mouse uridine phosphorylase polyclonal antibody was used. As is shown in FIG. 5, practically no band of uridine phosphorylase was detected in the uridine phosphorylase expression deficient mice.

Example 6
Blood Uridine Levels in the Intestines of Normal and Uridine Phosphorylase Expression Deficient Mice Blood samples were collected from normal and uridine phosphorylase expression deficient mice, respectively. From each blood sample, serum was separated, followed by the addition of 9 volumes of ice-cold methanol. The resulting mixture was left over in ice for 30 minutes to have proteins fully precipitated. The mixture was then centrifuged and, after the supernatant so obtained was caused to evaporate to dryness at 60° C. under a nitrogen gas stream, purified water (200 μL) was added to the residue. The thus-prepared mixture was filtered through a 0.45-μm filter. The concentrations of uridine, thymidine and cytidine were determined by HPLC. The results are presented in Table 2.

TABLE 2

| Mice | Uridine concentration (nmol/mL ± SD) | Thymidine concentration (nmol/mL ± SD) | Cytidine concentration (nmol/mL ± SD) |
|---|---|---|---|
| Non-recombinant (normal) mice | 5.33 ± 1.34 | 0.78 ± 0.05 | 6.00 ± 1.06 |
| Uridine phosphorylase expression deficient mice | 27.26 ± 2.78 | 1.35 ± 0.01 | 8.94 ± 0.69 |

As is shown in Table 2, the serum uridine level was 5.33 nmol/mL in the normal mice and 27.26 nmol/mL in the uridine phosphorylase expression deficient mice. An increase as much as about 5 times was therefore observed in the uridine phosphorylase expression deficient mice. Concerning the concentrations of thymidine and cytidine, the other blood nucleosides, only slight increases were observed in the uridine phosphorylase expression deficient mice than in the normal mice, and no substantial changes were confirmed by the knockout of the uridine phosphorylase expressing function.

Example 7

Metabolic Kinetics of Nucleoside Anticancer Agents in Normal and Uridine Phosphorylase Expression Deficient Mice Changes in the metabolic kinetics of nucleoside anticancer agents by the knockout of the uridine phosphorylase expressing function were investigated using 5-fluorouridine (FUR) and 5-trifluorothymidine ($F_3$dThd).

Normal and uridine phosphorylase expression deficient mice (n=3 per group) were orally administered with 50 mg/kg of FUR or 10 mg/kg of $F_3$dThd, and blood samples were collected with time. After serum was separated from each blood sample, the concentration of FUR or $F_3$dThd in the serum was determined by HPLC.

The results are presented in Table 3.

TABLE 3

| Mice | Time (min) | FUR concentration (nmol/mL ± SD) | F$_3$dThd concentration (nmol/mL ± SD) |
|---|---|---|---|
| Non-recombinant (normal) mice | 15 | 1.22 ± 0.12 | 16.61 ± 5.76 |
| | 30 | 1.26 ± 0.51 | 8.19 ± 4.29 |
| | 60 | 2.08 ± 0.98 | 2.64 ± 1.17 |
| | 120 | Not tested | 0.10 ± 0.08 |
| Uridine phosphorylase expression deficient mice | 15 | 5.95 ± 1.15 | 16.75 ± 2.94 |
| | 30 | 5.05 ± 2.48 | 13.42 ± 2.17 |
| | 60 | 3.33 ± 1.30 | 6.52 ± 5.24 |
| | 120 | Not tested | 1.78 ± 0.94 |

Each value is an average ± SD of n = 3.

As is shown in Table 3, when FUR was orally administered, the concentration of FUR in the uridine phosphorylase expression deficient mice was about 5 times as high as that in the normal mice (the values at 15 to 30 minutes after the administration). It has, therefore, been substantiated that as a result of the deletion of uridine phosphorylase activity, the decomposition of FUR in the body is inhibited. In the case of F$_3$dThd, on the other hand, the concentration of F$_3$dThd in the uridine phosphorylase expression deficient mice was also 1.6 to 17.8 times as high as the corresponding value in the normal mice from 30 minutes to 120 minutes after its oral administration. It was, hence, ascertained that the proportion of F$_3$dThd decomposed by uridine phosphorylase was reduced.

From the above results, mice deficient in the function of uridine phosphorylase genes are considered to be human-resembling models, and in connection with pyrimidine nucleoside anticancer agents, their metabolic kinetics in human are predictable from their metabolic kinetics in these mice.

INDUSTRIAL APPLICABILITY

By the present invention, genetically stable, uridine phosphorylase expression deficient animals can be obtained. These animals make it possible to elucidate pathologic functions or activities such as nucleic acid dysbolism and also to predict utility of pyrimidine nucleoside antimetabolites in human, and are useful as experimental animals.

What is claimed is:

1. A mouse comprising in its genome homozygous inactivated uridine phosphorylase gene locuses, or an offspring thereof, wherein said mouse is deficient in the expression of uridine phosphorylase and exhibits a decreased metabolism of a nucleotide anticancer agent or an antimetabolite, or both.

2. The mouse of claim 1 or an offspring thereof, wherein the function of said uridine phosphorylase gene has been rendered deficient by deleting a part of a DNA sequence of said uridine phosphorylase gene or by inserting or replacing another gene into or at a site of said DNA sequence.

3. The mouse of claim 2 or an offspring thereof, wherein said another gene is a marker gene or a reporter gene.

4. The mouse of claim 3, or an offspring thereof, comprising a marker gene that is a neomycin resistance gene.

5. The mouse of claim 1 or an offspring thereof comprising a mouse uridine phosphorylase gene with a neomycin resistance gene inserted in place of a second coding exon in said mouse uridine phosphorylase gene.

6. A method for measuring the kinetics of an anticancer agent or an antimetabolite comprising administering said anticancer agent or antimetabolite to the mouse of claim 1 and measuring the metabolic kinetics of said anticancer agent or antimetabolite.

7. The method of claim 6, wherein said anticancer agent or antimetabolite is a pyrimidine nucleoside.

8. A method for making a mouse comprising in its genome homozygous inactivated uridine phosphorylase gene locuses, wherein said mouse is deficient in the expression of uridine phosphorylase and exhibits a decreased metabolism of a nucleotide anticancer agent or an antimetabolite, or both, comprising:

mating two heterozygous mice each comprising an inactivated uridine phosphorylase gene, selecting an offspring comprising in its genome homozygous inactivated uridine phosphorylase gene locuses, which is deficient in the expression of uridine phosphorylase and which exhibits a decreased metabolism of a nucleotide anticancer agent or an antimetabolite, or both.

* * * * *